United States Patent
Zheng et al.

(10) Patent No.: US 10,883,092 B2
(45) Date of Patent: Jan. 5, 2021

(54) PHI29 DNA POLYMERASE AND ENCODING GENE AND APPLICATION THEREOF

(71) Applicant: MGI TECH CO., LTD., Shenzhen (CN)

(72) Inventors: Yue Zheng, Shenzhen (CN); Zhougang Zhang, Shenzhen (CN); Yuliang Dong, Shenzhen (CN); Wenwei Zhang, Shenzhen (CN); Chongjun Xu, Shenzhen (CN); Snezana Drmanac, Shenzhen (CN)

(73) Assignee: MGI TECH CO., LTD., Shenzhen (CN)

( * ) Notice: Subject to any disclaimer, the term of this patent is extended or adjusted under 35 U.S.C. 154(b) by 0 days.

(21) Appl. No.: 16/606,148

(22) PCT Filed: Apr. 18, 2017

(86) PCT No.: PCT/CN2017/080858
§ 371 (c)(1),
(2) Date: Oct. 17, 2019

(87) PCT Pub. No.: WO2018/191857
PCT Pub. Date: Oct. 25, 2018

(65) Prior Publication Data
US 2020/0048620 A1 Feb. 13, 2020

(51) Int. Cl.
*C12N 9/12* (2006.01)
*C12N 15/62* (2006.01)

(52) U.S. Cl.
CPC ............ *C12N 9/1252* (2013.01); *C12N 15/62* (2013.01); *C12Y 207/07007* (2013.01)

(58) Field of Classification Search
CPC ............ C12Y 207/07007; Y02P 20/52; C12Q 1/6827; C12Q 1/6869; C07K 2319/20; C12P 19/34; C12N 9/1252
See application file for complete search history.

(56) References Cited

U.S. PATENT DOCUMENTS

| | | | |
|---|---|---|---|
| 8,420,366 | B2 | 4/2013 | Clark et al. |
| 9,951,321 | B2 * | 4/2018 | Hanzel ............ C12Y 207/07007 |
| 2013/0217007 | A1 | 8/2013 | Kamtekar et al. |

FOREIGN PATENT DOCUMENTS

WO 2007075987 A3 1/2009

OTHER PUBLICATIONS

De Vega et al., Mutational analysis of phi29 DNA polymerase residues acting as ssDNA ligands for 3'-5' exonucleolysis. J. Mol. Biol., 1998, vol. 279: 807-882 (Year: 1998).*
Kisselev L., Polypeptide release factors in prokaryotes and eukaryotes: same function, different structure. Structure, 2002, vol. 10: 8-9. (Year: 2002).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): 26782-26785. (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Vega, M.D. et al., "Phage 29 DNA Polymerase Residues Involved in the Proper Stabilisation of the Primer-terminus at the 3'-5'Exonuciease Active Site" J. Mol. Biol. (2000) 304, 1-9.
Villegas, A.P. et al. "GenBank Accession No. YP_002004529" GenBank, Mar. 26, 2010, see the amino acid sequence and relevant information.
Reha-Krantz, L.J. "Are There Highly Conserved DNA Polymerase 3'_5' Exonuclease Motifs", Gene 112(1), Mar. 1, 1992, pp. 133-137.
International Search Report and Written Opinion issued for international application No. PCT/CN2017/080858, dated Jan. 19, 2018.

* cited by examiner

*Primary Examiner* — Ganapathirama Raghu
(74) *Attorney, Agent, or Firm* — Westman, Champlin & Koehler, P.A.; Z. Peter Sawicki; Amanda M. Prose

(57) ABSTRACT

Provided are a phi29 DNA polymerase and an encoding gene and an application thereof. The phi29 DNA polymerase is C1) or C2): C1) is a protein with DNA polymerase activity obtained by substituting at least one of the $58^{th}$, $61^{st}$, $94^{th}$, $96^{th}$, $119^{th}$, and $155^{th}$ amino acid residues in the amino acid sequence of a wild type phi29 DNA polymerase as shown in SEQ ID NO: 2 in the sequence listing; and C2) is a fusion protein obtained by linking a label to the N-terminus and/or C-terminus of the protein represented by C1). A 3'-5'exonuclease of the phi29 DNA polymerase has activity lower than that of the wild type phi29 DNA polymerase, and can efficiently and continuously synthesize DNA during amplification and sequencing.

3 Claims, 1 Drawing Sheet
Specification includes a Sequence Listing.

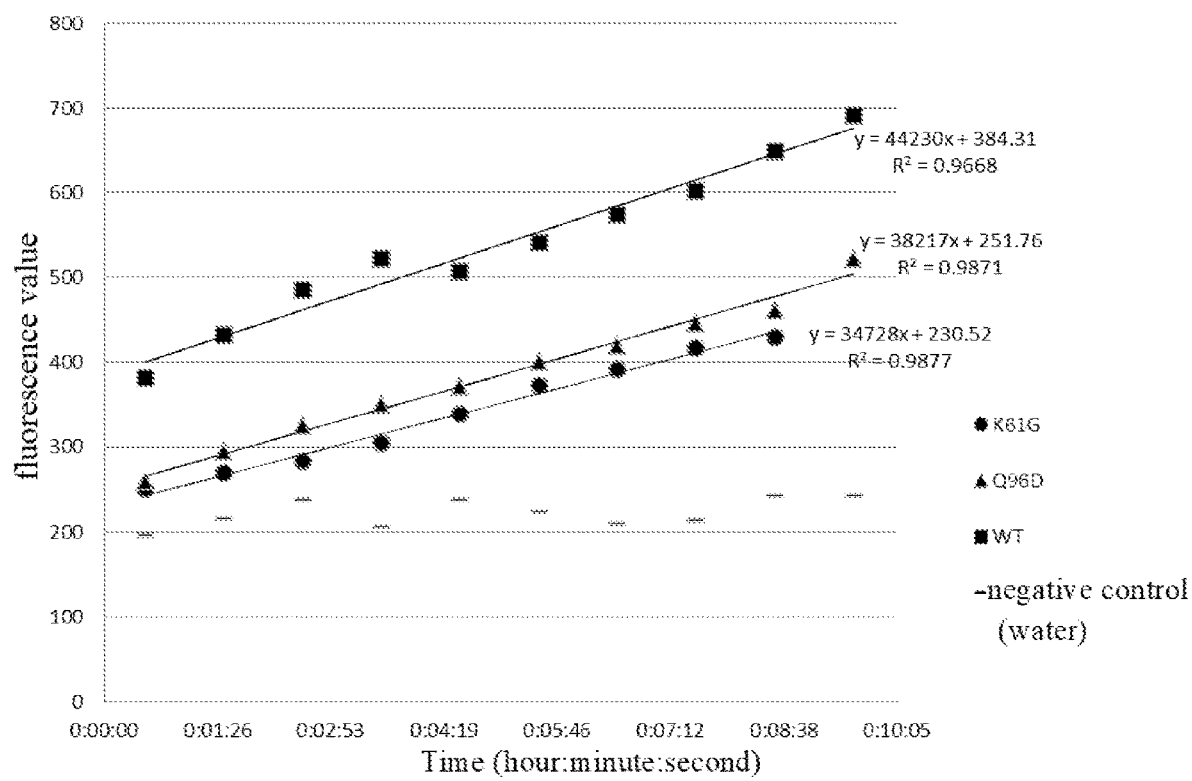

SEQUENCE LISTING

<160> NUMBER OF SEQ ID NOS: 4

<210> SEQ ID NO 1
<211> LENGTH: 1719
<212> TYPE: DNA
<213> ORGANISM: Artificial sequence
<220> FEATURE:
<223> OTHER INFORMATION: Nucleotide sequence encoding phi29 DNA polymerase

<400> SEQUENCE: 1

| | | | | | | |
|---|---|---|---|---|---|---|
| atgccgcgca | aaatgtatag | ctgcgacttt | gaaaccacca | ccaaagtgga | agattgccgc | 60 |
| gtttgggcgt | atggctatat | gaacatcgaa | gaccacagcg | aatacaaaat | tggcaacagc | 120 |
| ctggatgaat | ttatggcgtg | ggtgctgaaa | gttcaggcgg | atctgtattt | tcacaacctg | 180 |
| aaatttgacg | gcgcgttcat | tattaactgg | ctggaacgca | acggctttaa | atggagcgcg | 240 |
| gatggcttac | cgaacaccta | taacaccatt | attagccgca | tgggccagtg | gtatatgatt | 300 |
| gatatctgcc | tgggctataa | aggcaaacgc | aagattcata | ccgtgatcta | tgatagcctg | 360 |
| aagaaactgc | cgtttccggt | gaaaaaaatc | gcgaaggact | ttaaactgac | cgtgctgaaa | 420 |
| ggcgatattg | actaccataa | agaacgcccg | gtgggctata | aaattacccc | ggaggaatat | 480 |
| gcgtacatca | gaacgacat | ccagattatt | gcggaagcgc | tgctgattca | gtttaaacag | 540 |
| ggcctggatc | gtatgaccgc | gggtagcgat | agcctgaaag | ctttaaagga | cattatcacc | 600 |
| accaagaagt | tcaagaaagt | gtttccgacc | ctgagcctgg | gcctggataa | agaagtgcgc | 660 |
| tatgcgtatc | gcggtggctt | tacctggctg | aacgatcgct | taaggaaaa | ggaaattggc | 720 |
| gaaggcatgg | tgtttgatgt | gaacagcctg | tatccggcgc | agatgtatag | ccgcctgctg | 780 |
| ccgtatggtg | aaccgattgt | gtttgaaggc | aagtatgtgt | gggatgaaga | ttatccgctg | 840 |
| cacattcagc | atattcgctg | cgaattcgaa | ctgaaggaag | ctatattcc | gaccattcag | 900 |
| attaaacgca | ccgctttta | taaggcaac | gagtacctga | aaagcagcgg | cggcgaaatt | 960 |
| gcggatctgt | ggctgagcaa | cgtggatctg | gaactgatga | agaacacta | cgatctgtac | 1020 |
| aacgtggaat | atatcagcgg | cctgaaattt | aaagcgacca | ccggcctgtt | taaggacttt | 1080 |
| atcgacaagt | ggacctacat | taaaaccacc | agcgaaggcg | cgattaaaca | gctggcgaaa | 1140 |
| ctgatgctga | acagcctgta | tggcaaattt | gcgagcaacc | cggatgttac | cggcaaagtg | 1200 |
| ccgtatctga | agaaaacgg | cgcgctgggc | tttcgtttag | gcgaagagga | aaccaaagat | 1260 |
| ccggtgtata | ccccgatggg | cgtgtttatt | accgcgtggg | cgcgctatac | caccattacc | 1320 |
| gcggcgcagg | cgtgttatga | tcgcattatc | tattgcgata | ccgatagcat | tcatctgacc | 1380 |
| ggcaccgaaa | ttccggatgt | gatcaaagat | attgtggacc | cgaaaaaact | gggctattgg | 1440 |
| gcgcatgaaa | gcacctttaa | acgcgcgaaa | tatctgcgcc | agaaaaccta | tccaggac | 1500 |
| atctacatga | aagaggtgga | tggcaaactg | gttgaaggca | gcccggatga | ttataccgat | 1560 |
| attaagttca | gcgtgaaatg | cgcgggcatg | accgataaaa | ttaagaagga | agtgaccttc | 1620 |
| gagaacttta | aagtgggctt | tagccgcaaa | atgaaaccga | aaccggttca | ggtgcctggc | 1680 |
| ggtgttgttc | tggtggatga | taccttcacc | atcaagtga | | | 1719 |

<210> SEQ ID NO 2
<211> LENGTH: 572
<212> TYPE: PRT
<213> ORGANISM: Artificial sequence
<220> FEATURE:
<223> OTHER INFORMATION: Amino acid sequence of phi29 DNA polymerase

<400> SEQUENCE: 2

```
Met Pro Arg Lys Met Tyr Ser Cys Asp Phe Glu Thr Thr Thr Lys Val
1               5                   10                  15

Glu Asp Cys Arg Val Trp Ala Tyr Gly Tyr Met Asn Ile Glu Asp His
            20                  25                  30

Ser Glu Tyr Lys Ile Gly Asn Ser Leu Asp Glu Phe Met Ala Trp Val
        35                  40                  45

Leu Lys Val Gln Ala Asp Leu Tyr Phe His Asn Leu Lys Phe Asp Gly
    50                  55                  60

Ala Phe Ile Ile Asn Trp Leu Glu Arg Asn Gly Phe Lys Trp Ser Ala
65                  70                  75                  80

Asp Gly Leu Pro Asn Thr Tyr Asn Thr Ile Ile Ser Arg Met Gly Gln
                85                  90                  95

Trp Tyr Met Ile Asp Ile Cys Leu Gly Tyr Lys Gly Lys Arg Lys Ile
            100                 105                 110

His Thr Val Ile Tyr Asp Ser Leu Lys Lys Leu Pro Phe Pro Val Lys
        115                 120                 125

Lys Ile Ala Lys Asp Phe Lys Leu Thr Val Leu Lys Gly Asp Ile Asp
    130                 135                 140

Tyr His Lys Glu Arg Pro Val Gly Tyr Lys Ile Thr Pro Glu Glu Tyr
145                 150                 155                 160

Ala Tyr Ile Lys Asn Asp Ile Gln Ile Ala Glu Ala Leu Leu Ile
            165                 170                 175

Gln Phe Lys Gln Gly Leu Asp Arg Met Thr Ala Gly Ser Asp Ser Leu
        180                 185                 190

Lys Gly Phe Lys Asp Ile Ile Thr Thr Lys Lys Phe Lys Lys Val Phe
    195                 200                 205

Pro Thr Leu Ser Leu Gly Leu Asp Lys Glu Val Arg Tyr Ala Tyr Arg
210                 215                 220

Gly Gly Phe Thr Trp Leu Asn Asp Arg Phe Lys Glu Lys Glu Ile Gly
225                 230                 235                 240

Glu Gly Met Val Phe Asp Val Asn Ser Leu Tyr Pro Ala Gln Met Tyr
            245                 250                 255

Ser Arg Leu Leu Pro Tyr Gly Glu Pro Ile Val Phe Glu Gly Lys Tyr
        260                 265                 270

Val Trp Asp Glu Asp Tyr Pro Leu His Ile Gln His Ile Arg Cys Glu
    275                 280                 285

Phe Glu Leu Lys Glu Gly Tyr Ile Pro Thr Ile Gln Ile Lys Arg Ser
290                 295                 300

Arg Phe Tyr Lys Gly Asn Glu Tyr Leu Lys Ser Ser Gly Gly Glu Ile
305                 310                 315                 320

Ala Asp Leu Trp Leu Ser Asn Val Asp Leu Glu Leu Met Lys Glu His
            325                 330                 335

Tyr Asp Leu Tyr Asn Val Glu Tyr Ile Ser Gly Leu Lys Phe Lys Ala
        340                 345                 350

Thr Thr Gly Leu Phe Lys Asp Phe Ile Asp Lys Trp Thr Tyr Ile Lys
    355                 360                 365

Thr Thr Ser Glu Gly Ala Ile Lys Gln Leu Ala Lys Leu Met Leu Asn
370                 375                 380

Ser Leu Tyr Gly Lys Phe Ala Ser Asn Pro Asp Val Thr Gly Lys Val
385                 390                 395                 400

Pro Tyr Leu Lys Glu Asn Gly Ala Leu Gly Phe Arg Leu Gly Glu Glu
            405                 410                 415
```

```
Glu Thr Lys Asp Pro Val Tyr Thr Pro Met Gly Val Phe Ile Thr Ala
                420                 425                 430

Trp Ala Arg Tyr Thr Thr Ile Thr Ala Ala Gln Ala Cys Tyr Asp Arg
            435                 440                 445

Ile Ile Tyr Cys Asp Thr Asp Ser Ile His Leu Thr Gly Thr Glu Ile
        450                 455                 460

Pro Asp Val Ile Lys Asp Ile Val Asp Pro Lys Lys Leu Gly Tyr Trp
465                 470                 475                 480

Ala His Glu Ser Thr Phe Lys Arg Ala Lys Tyr Leu Arg Gln Lys Thr
                    485                 490                 495

Tyr Ile Gln Asp Ile Tyr Met Lys Glu Val Asp Gly Lys Leu Val Glu
                500                 505                 510

Gly Ser Pro Asp Asp Tyr Thr Asp Ile Lys Phe Ser Val Lys Cys Ala
            515                 520                 525

Gly Met Thr Asp Lys Ile Lys Lys Glu Val Thr Phe Glu Asn Phe Lys
        530                 535                 540

Val Gly Phe Ser Arg Lys Met Lys Pro Lys Pro Val Gln Val Pro Gly
545                 550                 555                 560

Gly Val Val Leu Val Asp Asp Thr Phe Thr Ile Lys
                565                 570
```

<210> SEQ ID NO 3
<211> LENGTH: 1779
<212> TYPE: DNA
<213> ORGANISM: Artificial sequence
<220> FEATURE:
<223> OTHER INFORMATION: Fusion gene encoding fusion protein 1

<400> SEQUENCE: 3

| | | |
|---|---|---|
| atgggcagca gccatcatca tcatcatcac agcagcggcc tggtgccgcg cggcagccat | 60 |
| atgccgcgca aaatgtatag ctgcgacttt gaaaccacca ccaaagtgga agattgccgc | 120 |
| gtttgggcgt atggctatat gaacatcgaa gaccacagca atacaaaat tggcaacagc | 180 |
| ctggatgaat ttatggcgtg ggtgctgaaa gttcaggcgg atctgtattt tcacaacctg | 240 |
| aaatttgacg gcgcgttcat tattaactgg ctggaacgca cggctttaa atggagcgcg | 300 |
| gatggcttac cgaacaccta taacaccatt attagccgca tgggccagtg gtatatgatt | 360 |
| gatatctgcc tgggctataa aggcaaacgc aagattcata ccgtgatcta tgatagcctg | 420 |
| aagaaactgc cgtttccggt gaaaaaaatc gcgaaggact ttaaactgac cgtgctgaaa | 480 |
| ggcgatattg actaccataa agaacgcccg gtgggctata aaattccccc ggaggaatat | 540 |
| gcgtacatca gaacgacat ccagattatt gcggaagcgc tgctgattca gtttaaacag | 600 |
| ggcctggatc gtatgaccgc gggtagcgat agcctgaaag ctttaaggga cattatcacc | 660 |
| accaagaagt tcaagaaagt gtttccgacc ctgagcctgg gcctggataa agaagtgcgc | 720 |
| tatgcgtatc gcggtggctt tacctggctg aacgatcgct ttaaggaaaa ggaaattggc | 780 |
| gaaggcatgg tgtttgatgt gaacagcctg tatccggcgc agatgtatag ccgcctgctg | 840 |
| ccgtatggtg aaccgattgt gtttgaaggc aagtatgtgt gggatgaaga ttatccgctg | 900 |
| cacattcagc atattcgctg cgaattcgaa ctgaaggaag ctatattcc gaccattcag | 960 |
| attaaacgca gccgctttta taaaggcaac gagtacctga aaagcagcgg cggcgaaatt | 1020 |
| gcggatctgt ggctgagcaa cgtggatctg aactgatga agaacactta cgatctgtac | 1080 |
| aacgtggaat atatcagcgg cctgaaattt aaagcgacca ccggcctgtt taaggacttt | 1140 |

```
atcgacaagt ggacctacat taaaaccacc agcgaaggcg cgattaaaca gctggcgaaa    1200
ctgatgctga acagcctgta tggcaaattt gcgagcaacc cggatgttac cggcaaagtg    1260
ccgtatctga agaaaacgg cgcgctgggc tttcgtttag gcgaagagga aaccaaagat    1320
ccggtgtata ccccgatggg cgtgtttatt accgcgtggg cgcgctatac caccattacc    1380
gcggcgcagg cgtgttatga tcgcattatc tattgcgata ccgatagcat tcatctgacc    1440
ggcaccgaaa ttccggatgt gatcaaagat attgtggacc cgaaaaaact gggctattgg    1500
gcgcatgaaa gcacctttaa acgcgcgaaa tatctgcgcc agaaaaccta tccaggac    1560 atctacatga agaggtgga tggcaaactg gttgaaggca gcccggatga ttataccgat    1620
attaagttca gcgtgaaatg cgcgggcatg accgataaaa ttaagaagga agtgaccttc    1680 gagaactta aagtgggctt tagccgcaaa atgaaaccga aaccggttca ggtgcctggc    1740
ggtgttgttc tggtggatga taccttcacc atcaagtga                          1779
```

<210> SEQ ID NO 4
<211> LENGTH: 592
<212> TYPE: PRT
<213> ORGANISM: Artificial sequence
<220> FEATURE:
<223> OTHER INFORMATION: Fusion protein 1 containing His-tag

<400> SEQUENCE: 4

```
Met Gly Ser Ser His His His His His Ser Ser Gly Leu Val Pro
1               5                   10                  15

Arg Gly Ser His Met Pro Arg Lys Met Tyr Ser Cys Asp Phe Glu Thr
            20                  25                  30

Thr Thr Lys Val Glu Asp Cys Arg Val Trp Ala Tyr Gly Tyr Met Asn
        35                  40                  45

Ile Glu Asp His Ser Glu Tyr Lys Ile Gly Asn Ser Leu Asp Glu Phe
    50                  55                  60

Met Ala Trp Val Leu Lys Val Gln Ala Asp Leu Tyr Phe His Asn Leu
65                  70                  75                  80

Lys Phe Asp Gly Ala Phe Ile Ile Asn Trp Leu Glu Arg Asn Gly Phe
                85                  90                  95

Lys Trp Ser Ala Asp Gly Leu Pro Asn Thr Tyr Asn Thr Ile Ile Ser
            100                 105                 110

Arg Met Gly Gln Trp Tyr Met Ile Asp Ile Cys Leu Gly Tyr Lys Gly
        115                 120                 125

Lys Arg Lys Ile His Thr Val Ile Tyr Asp Ser Leu Lys Lys Leu Pro
    130                 135                 140

Phe Pro Val Lys Lys Ile Ala Lys Asp Phe Lys Leu Thr Val Leu Lys
145                 150                 155                 160

Gly Asp Ile Asp Tyr His Lys Glu Arg Pro Val Gly Tyr Lys Ile Thr
                165                 170                 175

Pro Glu Glu Tyr Ala Tyr Ile Lys Asn Asp Ile Gln Ile Ile Ala Glu
            180                 185                 190

Ala Leu Leu Ile Gln Phe Lys Gln Gly Leu Asp Arg Met Thr Ala Gly
        195                 200                 205

Ser Asp Ser Leu Lys Gly Phe Lys Asp Ile Ile Thr Thr Lys Lys Phe
    210                 215                 220

Lys Lys Val Phe Pro Thr Leu Ser Leu Gly Leu Asp Lys Glu Val Arg
225                 230                 235                 240

Tyr Ala Tyr Arg Gly Gly Phe Thr Trp Leu Asn Asp Arg Phe Lys Glu
                245                 250                 255
```

```
Lys Glu Ile Gly Glu Gly Met Val Phe Asp Val Asn Ser Leu Tyr Pro
            260             265             270

Ala Gln Met Tyr Ser Arg Leu Leu Pro Tyr Gly Glu Pro Ile Val Phe
        275             280             285

Glu Gly Lys Tyr Val Trp Asp Glu Asp Tyr Pro Leu His Ile Gln His
        290             295             300

Ile Arg Cys Glu Phe Glu Leu Lys Glu Gly Tyr Ile Pro Thr Ile Gln
305             310             315             320

Ile Lys Arg Ser Arg Phe Tyr Lys Gly Asn Glu Tyr Leu Lys Ser Ser
                325             330             335

Gly Gly Glu Ile Ala Asp Leu Trp Leu Ser Asn Val Asp Leu Glu Leu
            340             345             350

Met Lys Glu His Tyr Asp Leu Tyr Asn Val Glu Tyr Ile Ser Gly Leu
            355             360             365

Lys Phe Lys Ala Thr Thr Gly Leu Phe Lys Asp Phe Ile Asp Lys Trp
    370             375             380

Thr Tyr Ile Lys Thr Thr Ser Glu Gly Ala Ile Lys Gln Leu Ala Lys
385             390             395             400

Leu Met Leu Asn Ser Leu Tyr Gly Lys Phe Ala Ser Asn Pro Asp Val
            405             410             415

Thr Gly Lys Val Pro Tyr Leu Lys Glu Asn Gly Ala Leu Gly Phe Arg
            420             425             430

Leu Gly Glu Glu Glu Thr Lys Asp Pro Val Tyr Thr Pro Met Gly Val
            435             440             445

Phe Ile Thr Ala Trp Ala Arg Tyr Thr Thr Ile Thr Ala Ala Gln Ala
    450             455             460

Cys Tyr Asp Arg Ile Ile Tyr Cys Asp Thr Asp Ser Ile His Leu Thr
465             470             475             480

Gly Thr Glu Ile Pro Asp Val Ile Lys Asp Ile Val Asp Pro Lys Lys
            485             490             495

Leu Gly Tyr Trp Ala His Glu Ser Thr Phe Lys Arg Ala Lys Tyr Leu
            500             505             510

Arg Gln Lys Thr Tyr Ile Gln Asp Ile Tyr Met Lys Glu Val Asp Gly
        515             520             525

Lys Leu Val Glu Gly Ser Pro Asp Asp Tyr Thr Asp Ile Lys Phe Ser
    530             535             540

Val Lys Cys Ala Gly Met Thr Asp Lys Ile Lys Lys Glu Val Thr Phe
545             550             555             560

Glu Asn Phe Lys Val Gly Phe Ser Arg Lys Met Lys Pro Lys Pro Val
            565             570             575

Gln Val Pro Gly Gly Val Val Leu Val Asp Asp Thr Phe Thr Ile Lys
            580             585             590
```

PHI29 DNA POLYMERASE AND ENCODING GENE AND APPLICATION THEREOF

CROSS-REFERENCE TO RELATED APPLICATION

This application is the U.S. national phase of PCT Application No. PCT/CN2017/080858 filed on Apr. 18, 2017, the entire content of which is incorporated herein by reference.

FIELD

The present disclosure relates to the field of biotechnology, in particular to phi29 DNA polymerase and encoding gene as well as application thereof.

BACKGROUND

Phi29 DNA polymerase is a mesophilic DNA polymerase from *Bacillus subtilis* phage Phi29, which can be obtained through expression of its encoding gene in *Escherichia coli* via genetic recombination technology followed by several purification processes. Phi29 DNA polymerase comprises 572 amino acids, with a 3'-5'exonuclease active site and a strand-displacement active site in its amino terminal region (i.e. the N-terminus) and a DNA-amplification active site in its carboxy-terminal region (i.e. the C-terminus), where the DNA-amplification active site can be initiated by a protein or DNA. Such a phi29 DNA polymerase has effective and persistent DNA-replicating ability thus being useful in isothermal amplification, whole-genome amplification under random primers, rolling circle amplification and the like; as well as exhibits 3'-5'exonuclease proofreading activity, with a high fidelity. The phi29 DNA polymerase displays its 3'-5'exonuclease activity by continuously cutting the single-stranded DNA substrate longer than 6 nucleotides in the presence of $Mg^{2+}$ ions as a metal ion activator at a catalytic constant of 500 $s^{-1}$. However, the dissociation rate between the phi29 DNA polymerase and the single-stranded DNA substrate drops to 1 $s^{-1}$ when the single-stranded DNAs are in a length of 4 to 6 nucleotides.

Though ensuring a high fidelity, the 3'-5'exonuclease proofreading activity of phi29 DNA polymerase can cause side effects, such as primer degradation. Thus, when phi29 DNA polymerase is used for amplification and sequencing, the concentration of primers in the system will be decreased which can directly affect the reaction efficiency, on the other hand the primers in the system will be cleaved into different lengths due to the phi29 DNA polymerase, thereby reducing the binding specificity between primers and target sequences.

For phi29 DNA polymerase, its functional domains involving in 3'-5'exonuclease activity are mainly located in Exo-I, Exo-II and Exo-III motifs in the N-terminus, where amino acid residues, such as aspartic acid at position 12 (D12), glutamic acid at position 14 (E14), aspartic acid at position 66 (D66), tyrosine at position 165 (Y165), aspartic acid at position 169 (D169) and the like are critical for the efficacy of 3'-5'exonuclease activity according to the steady-state analysis. However, the amino acid residues (e.g. D12, D66, Y165, D169 and the like) also closely related to the strand-displacement function of phi29 DNA polymerase apart from being central active sites of 3'-5'exonuclease activity, thus their mutations will change the strand-displacement activity of phi29 DNA polymerase. It is found that the amino acid mutations like T15I mutation (i.e. mutation of threonine at position 15 into isoleucine) or N62D mutation (i.e. mutation of asparagine at position 62 into aspartic acid) can reduce the 3'-5'exonuclease activity of phi29 DNA polymerase significantly while remaining the strand-displacement activity, however the phi29 DNA polymerase variant with T15I or N62D mutation will tolerate the insertion of mismatched nucleotides due to greatly reduced ability of stabilizing single-stranded DNA, thus exhibiting largely lowed fidelity. Therefore, there is an urgent need to develop a favorable phi29 DNA polymerase variant with decreased side effects owing to reduced 3'-5'exonuclease activity and unchanged fidelity, thereby improving the effectiveness and universality in applications such as amplification, sequencing and the like.

The current method for determining the 3'-5'exonuclease activity of phi29 DNA polymerase is based on radioisotope-labelled DNA substrate, with a high accuracy but still with problems of high-cost and safety concern.

SUMMARY

Embodiments of the present disclosure seek to solve at least one of the problems existing in the related art by providing a DNA polymerase having reduced 3'-5'exonuclease activity, so as to increase the reaction efficiency at amplification and sequencing.

For this, the present disclosure in embodiments provides a protein.

The protein provided in embodiments is selected from protein C1) or C2), wherein C1) has at least one amino acid substitution(s) at positions 61, 96, 58, 94, 119 or 155 relative to the amino acid sequence of phi29 DNA polymerase, wherein the protein has DNA polymerase activity; and C2) is a fusion protein formed by ligating with a tag at the N-terminus or/and the C-terminus of the protein C1).

Among the proteins as described above, the phi29 DNA polymerase has an amino acid sequence as shown in SEQ ID NO: 2 in the sequence listing.

Among the proteins as described above, the lysine residue at position 61 can be substituted with a glycine residue or an arginine residue; the methionine residue at position 94 can be substituted with a lysine residue; the histidine residue at position 58 can be substituted with an alanine residue; the glutamine residue at position 96 can be substituted with an aspartic acid residue; the serine residue at position 119 can be substituted with an alanine residue; and the isoleucine residue at position 155 can be substituted with an arginine residue.

Among the proteins as described above, the protein has reduced exonuclease activity compared to the phi29 DNA polymerase, where the exonuclease activity is 3'-5'exonuclease activity.

Specifically, the protein as described above is any one selected from protein a1 to protein a48.

Protein a1 is a protein obtained by substituting the histidine residue at position 58 from the N-terminus with an alanine residue relative to the amino acid sequence as shown in SEQ ID NO: 2 in the sequence listing.

Protein a2 is a protein obtained by substituting the lysine residue at position 61 from the N-terminus with a glycine residue relative to the amino acid sequence as shown in SEQ ID NO: 2 in the sequence listing.

Protein a3 is a protein obtained by substituting the lysine residue at position 61 from the N-terminus with an arginine residue relative to the amino acid sequence as shown in SEQ ID NO: 2 in the sequence listing.

Protein a4 is a protein obtained by substituting the glutamine residue at position 96 from the N-terminus with an aspartic acid residue relative to the amino acid sequence as shown in SEQ ID NO: 2 in the sequence listing.

Protein a5 is a protein obtained by substituting the serine residue at position 119 from the N-terminus with an alanine residue relative to the amino acid sequence as shown in SEQ ID NO: 2 in the sequence listing.

Protein a6 is a protein obtained by substituting the histidine residue at position 58 from the N-terminus with an alanine residue and the lysine residue at position 61 from the N-terminus with a glycine residue relative to the amino acid sequence as shown in SEQ ID NO: 2 in the sequence listing.

Protein a7 is a protein obtained by substituting the histidine residue at position 58 from the N-terminus with an alanine residue and the lysine residue at position 61 from the N-terminus with an arginine residue relative to the amino acid sequence as shown in SEQ ID NO: 2 in the sequence listing.

Protein a8 is a protein obtained by substituting the histidine residue at position 58 from the N-terminus with an alanine residue and the glutamine residue at position 96 from the N-terminus with an aspartic acid residue relative to the amino acid sequence as shown in SEQ ID NO: 2 in the sequence listing.

Protein a9 is a protein obtained by substituting the histidine residue at position 58 from the N-terminus with an alanine residue and the serine residue at position 119 from the N-terminus with an alanine residue relative to the amino acid sequence as shown in SEQ ID NO: 2 in the sequence listing.

Protein a10 is a protein obtained by substituting the lysine residue at position 61 from the N-terminus with a glycine residue and the glutamine residue at position 96 from the N-terminus with an aspartic acid residue relative to the amino acid sequence as shown in SEQ ID NO: 2 in the sequence listing.

Protein a11 is a protein obtained by substituting the lysine residue at position 61 from the N-terminus with a glycine residue and the serine residue at position 119 from the N-terminus with an alanine residue relative to the amino acid sequence as shown in SEQ ID NO: 2 in the sequence listing.

Protein a12 is a protein obtained by substituting the lysine residue at position 61 from the N-terminus with an arginine residue and the glutamine residue at position 96 from the N-terminus with an aspartic acid residue relative to the amino acid sequence as shown in SEQ ID NO: 2 in the sequence listing.

Protein a13 is a protein obtained by substituting the lysine residue at position 61 from the N-terminus with an arginine residue and the serine residue at position 119 from the N-terminus with an alanine residue relative to the amino acid sequence as shown in SEQ ID NO: 2 in the sequence listing.

Protein a14 is a protein obtained by substituting the glutamine residue at position 96 from the N-terminus with an aspartic acid residue and the serine residue at position 119 from the N-terminus with an alanine residue relative to the amino acid sequence as shown in SEQ ID NO: 2 in the sequence listing.

Protein a15 is a protein obtained by substituting the histidine residue at position 58 from the N-terminus with an alanine residue, the lysine residue at position 61 from the N-terminus with a glycine residue and the glutamine residue at position 96 from the N-terminus with an aspartic acid residue relative to the amino acid sequence as shown in SEQ ID NO: 2 in the sequence listing.

Protein a16 is a protein obtained by substituting the histidine residue at position 58 from the N-terminus with an alanine residue, the lysine residue at position 61 from the N-terminus with a glycine residue and the serine residue at position 119 from the N-terminus with an alanine residue relative to the amino acid sequence as shown in SEQ ID NO: 2 in the sequence listing.

Protein a17 is a protein obtained by substituting the histidine residue at position 58 from the N-terminus with an alanine residue, the lysine residue at position 61 from the N-terminus with an arginine residue and the glutamine residue at position 96 from the N-terminus with an aspartic acid residue relative to the amino acid sequence as shown in SEQ ID NO: 2 in the sequence listing.

Protein a18 is a protein obtained by substituting the histidine residue at position 58 from the N-terminus with an alanine residue, the lysine residue at position 61 from the N-terminus with an arginine residue and the serine residue at position 119 from the N-terminus with an alanine residue relative to the amino acid sequence as shown in SEQ ID NO: 2 in the sequence listing.

Protein a19 is a protein obtained by substituting the lysine residue at position 61 from the N-terminus with a glycine residue, the glutamine residue at position 96 from the N-terminus with an aspartic acid residue and the serine residue at position 119 from the N-terminus with an alanine residue relative to the amino acid sequence as shown in SEQ ID NO: 2 in the sequence listing.

Protein a20 is a protein obtained by substituting the lysine residue at position 61 from the N-terminus with an arginine residue, the glutamine residue at position 96 from the N-terminus with an aspartic acid residue and the serine residue at position 119 from the N-terminus with an alanine residue relative to the amino acid sequence as shown in SEQ ID NO: 2 in the sequence listing.

Protein a21 is a protein obtained by substituting the histidine residue at position 58 from the N-terminus with an alanine residue, the lysine residue at position 61 from the N-terminus with a glycine residue, the glutamine residue at position 96 from the N-terminus with an aspartic acid residue and the serine residue at position 119 from the N-terminus with an alanine residue relative to the amino acid sequence as shown in SEQ ID NO: 2 in the sequence listing.

Protein a22 is a protein obtained by substituting the histidine residue at position 58 from the N-terminus with an alanine residue, the lysine residue at position 61 from the N-terminus with an arginine residue, the glutamine residue at position 96 from the N-terminus with an aspartic acid residue, and the serine residue at position 119 from the N-terminus with an alanine residue relative to the amino acid sequence as shown in SEQ ID NO: 2 in the sequence listing.

Protein a23 is a protein obtained by substituting the methionine residue at position 94 from the N-terminus with a lysine residue relative to the amino acid sequence as shown in SEQ ID NO: 2 in the sequence listing.

Protein a24 is a protein obtained by substituting the isoleucine residue at position 155 from the N-terminus with an arginine residue relative to the amino acid sequence as shown in SEQ ID NO: 2 in the sequence listing.

Protein a25 is a protein obtained by substituting the histidine residue at position 78 from the N-terminus with an alanine residue relative to the amino acid sequence as shown in SEQ ID NO: 4 in the sequence listing.

Protein a26 is a protein obtained by substituting the lysine residue at position 81 from the N-terminus with a glycine residue relative to the amino acid sequence as shown in SEQ ID NO: 4 in the sequence listing.

Protein a27 is a protein obtained by substituting the lysine residue at position 81 from the N-terminus with an arginine residue relative to the amino acid sequence as shown in SEQ ID NO: 4 in the sequence listing.

Protein a28 is a protein obtained by substituting the glutamine residue at position 116 from the N-terminus with an aspartic acid residue relative to the amino acid sequence as shown in SEQ ID NO: 4 in the sequence listing.

Protein a29 is a protein obtained by substituting the serine residue at position 139 from the N-terminus with an alanine residue relative to the amino acid sequence as shown in SEQ ID NO: 4 in the sequence listing.

Protein a30 is a protein obtained by substituting the histidine residue at position 78 from the N-terminus with an alanine residue and the lysine residue at position 81 from the N-terminus with a glycine residue relative to the amino acid sequence as shown in SEQ ID NO: 4 in the sequence listing.

Protein a31 is a protein obtained by substituting the histidine residue at position 78 from the N-terminus with an alanine residue and the lysine residue at position 81 from the N-terminus with an arginine residue relative to the amino acid sequence as shown in SEQ ID NO: 4 in the sequence listing.

Protein a32 is a protein obtained by substituting the histidine residue at position 78 from the N-terminus with an alanine residue and the glutamine residue at position 116 from the N-terminus with an aspartic acid residue relative to the amino acid sequence as shown in SEQ ID NO: 4 in the sequence listing.

Protein a33 is a protein obtained by substituting the histidine residue at position 78 from the N-terminus with an alanine residue and the serine residue at position 139 from the N-terminus with an alanine residue relative to the amino acid sequence as shown in SEQ ID NO: 4 in the sequence listing.

Protein a34 is a protein obtained by substituting the lysine residue at position 81 from the N-terminus with a glycine residue and the glutamine residue at position 116 from the N-terminus with an aspartic acid residue relative to the amino acid sequence as shown in SEQ ID NO: 4 in the sequence listing.

Protein a35 is a protein obtained by substituting the lysine residue at position 81 from the N-terminus with a glycine residue and the serine residue at position 139 from the N-terminus with an alanine residue relative to the amino acid sequence as shown in SEQ ID NO: 4 in the sequence listing.

Protein a36 is a protein obtained by substituting the lysine residue at position 81 from the N-terminus with an arginine residue and the glutamine residue at position 116 from the N-terminus with an aspartic acid residue relative to the amino acid sequence as shown in SEQ ID NO: 4 in the sequence listing.

Protein a37 is a protein obtained by substituting the lysine residue at position 81 from the N-terminus with an arginine residue and the serine residue at position 139 from the N-terminus with an alanine residue relative to the amino acid sequence as shown in SEQ ID NO: 4 in the sequence listing.

Protein a38 is a protein obtained by substituting the glutamine residue at position 116 from the N-terminus with an aspartic acid residue and the serine residue at position 139 from the N-terminus with an alanine residue relative to the amino acid sequence as shown in SEQ ID NO: 4 in the sequence listing.

Protein a39 is a protein obtained by substituting the histidine residue at position 78 from the N-terminus with an alanine residue, the lysine residue at position 81 from the N-terminus with a glycine residue and the glutamine residue at position 116 from the N-terminus with an aspartic acid residue relative to the amino acid sequence as shown in SEQ ID NO: 4 in the sequence listing.

Protein a40 is a protein obtained by substituting the histidine residue at position 78 from the N-terminus with an alanine residue, the lysine residue at position 81 from the N-terminus with a glycine residue and the serine residue at position 139 from the N-terminus with an alanine residue relative to the amino acid sequence as shown in SEQ ID NO: 4 in the sequence listing.

Protein a41 is a protein obtained by substituting the histidine residue at position 78 from the N-terminus with an alanine residue, the lysine residue at position 81 from the N-terminus with an arginine residue and the glutamine residue at position 116 from the N-terminus with an aspartic acid residue relative to the amino acid sequence as shown in SEQ ID NO: 4 in the sequence listing.

Protein a42 is a protein obtained by substituting the histidine residue at position 78 from the N-terminus with an alanine residue, the lysine residue at position 81 from the N-terminus with an arginine residue and the serine residue at position 139 from the N-terminus with an alanine residue relative to the amino acid sequence as shown in SEQ ID NO: 4 in the sequence listing.

Protein a43 is a protein obtained by substituting the lysine residue at position 81 from the N-terminus with a glycine residue, the glutamine residue at position 116 from the N-terminus with an aspartic acid residue and the serine residue at position 139 from the N-terminus with an alanine residue relative to the amino acid sequence as shown in SEQ ID NO: 4 in the sequence listing.

Protein a44 is a protein obtained by substituting the lysine residue at position 81 from the N-terminus with an arginine residue, the glutamine residue at position 116 from the N-terminus with an aspartic acid residue and the serine residue at position 139 from the N-terminus with an alanine residue relative to the amino acid sequence as shown in SEQ ID NO: 4 in the sequence listing.

Protein a45 is a protein obtained by substituting the histidine residue at position 78 from the N-terminus with an alanine residue, the lysine residue at position 81 from the N-terminus with a glycine residue, the glutamine residue at position 116 from the N-terminus with an aspartic acid residue and the serine residue at position 139 from the N-terminus with an alanine residue relative to the amino acid sequence as shown in SEQ ID NO: 4 in the sequence listing.

Protein a46 is a protein obtained by substituting the histidine residue at position 78 from the N-terminus with an alanine residue, the lysine residue at position 81 from the N-terminus with an arginine residue, the glutamine residue at position 116 from the N-terminus with an aspartic acid residue and the serine residue at position 139 from the N-terminus with an alanine residue relative to the amino acid sequence as shown in SEQ ID NO: 4 in the sequence listing.

Protein a47 is a protein obtained by substituting the methionine residue at position 114 from the N-terminus with a lysine residue relative to the amino acid sequence as shown in SEQ ID NO: 4 in the sequence listing.

Protein a48 is a protein obtained by substituting the isoleucine residue at position 175 from the N-terminus with an arginine residue relative to the amino acid sequence as shown in SEQ ID NO: 4 in the sequence listing.

Nucleic acid molecules encoding any one of the proteins as described above are also within the scope of the present disclosure.

The nucleic acid molecule encoding individual proteins as described above may be specifically selected from DNA molecule b1 to DNA molecule b48.

DNA molecule b1 is a DNA molecule encoding the protein a1.

DNA molecule b2 is a DNA molecule encoding the protein a2.

DNA molecule b3 is a DNA molecule encoding the protein a3.

DNA molecule b4 is a DNA molecule encoding the protein a4.

DNA molecule b5 is a DNA molecule encoding the protein a5.

DNA molecule b6 is a DNA molecule encoding the protein a6.

DNA molecule b7 is a DNA molecule encoding the protein a7.

DNA molecule b8 is a DNA molecule encoding the protein a8.

DNA molecule b9 is a DNA molecule encoding the protein a9.

DNA molecule b10 is a DNA molecule encoding the protein a1°.

DNA molecule b11 is a DNA molecule encoding the protein a11.

DNA molecule b12 is a DNA molecule encoding the protein a12.

DNA molecule b13 is a DNA molecule encoding the protein a13.

DNA molecule b14 is a DNA molecule encoding the protein a14.

DNA molecule b15 is a DNA molecule encoding the protein a15.

DNA molecule b16 is a DNA molecule encoding the protein a16.

DNA molecule b17 is a DNA molecule encoding the protein a17.

DNA molecule b18 is a DNA molecule encoding the protein a18.

DNA molecule b19 is a DNA molecule encoding the protein a19.

DNA molecule b20 is a DNA molecule encoding the protein a20.

DNA molecule b21 is a DNA molecule encoding the protein a21.

DNA molecule b22 is a DNA molecule encoding the protein a22.

DNA molecule b23 is a DNA molecule encoding the protein a23.

DNA molecule b24 is a DNA molecule encoding the protein a24.

DNA molecule b25 is a DNA molecule encoding the protein a25.

DNA molecule b26 is a DNA molecule encoding the protein a26.

DNA molecule b27 is a DNA molecule encoding the protein a27.

DNA molecule b28 is a DNA molecule encoding the protein a28.

DNA molecule b29 is a DNA molecule encoding the protein a29.

DNA molecule b30 is a DNA molecule encoding the protein a30.

DNA molecule b31 is a DNA molecule encoding the protein a31.

DNA molecule b32 is a DNA molecule encoding the protein a32.

DNA molecule b33 is a DNA molecule encoding the protein a33.

DNA molecule b34 is a DNA molecule encoding the protein a34.

DNA molecule b35 is a DNA molecule encoding the protein a35.

DNA molecule b36 is a DNA molecule encoding the protein a36.

DNA molecule b37 is a DNA molecule encoding the protein a37.

DNA molecule b38 is a DNA molecule encoding the protein a38.

DNA molecule b39 is a DNA molecule encoding the protein a39.

DNA molecule b40 is a DNA molecule encoding the protein a40.

DNA molecule b41 is a DNA molecule encoding the protein a41.

DNA molecule b42 is a DNA molecule encoding the protein a42.

DNA molecule b43 is a DNA molecule encoding the protein a43.

DNA molecule b44 is a DNA molecule encoding the protein a44.

DNA molecule b45 is a DNA molecule encoding the protein a45.

DNA molecule b46 is a DNA molecule encoding the protein a46.

DNA molecule b47 is a DNA molecule encoding the protein a47.

DNA molecule b48 is a DNA molecule encoding the protein a48.

An expression cassette, a recombinant vector, a recombinant microorganism or a transgenic cell line comprising the nucleic acid molecule as described above are also within the scope of the present disclosure.

The recombinant vector may be a recombinant plasmid obtained by inserting the nucleic acid molecule as described above into an expression vector or a cloning vector. Specifically, the expression vector may be vector pET28a (+) proposed in examples.

Specifically, the recombinant vector may be recombinant plasmid pET28a-H58A, recombinant plasmid pET28a-K61G, recombinant plasmid pET28a-K61R, recombinant plasmid pET28a-Q96D, recombinant plasmid pET28a-S119A, recombinant plasmid pET28a-H58AK61G, recombinant plasmid pET28a-H58AK61R, recombinant plasmid pET28a-H58AQ96D, recombinant plasmid pET28a-H58AS119A, recombinant plasmid pET28a-K61GQ96D, recombinant plasmid pET28a-K61GS119A, recombinant plasmid pET28a-K61RQ96D, recombinant plasmid pET28a-K61RS119A, recombinant plasmid pET28a-Q96DS119A, recombinant plasmid pET28a-H58AK61GQ96D, recombinant plasmid pET28a-H58AK61GS119A, recombinant plasmid pET28a-H58AK61RQ96D, recombinant plasmid pET28a-H58AK61RS119A, recombinant plasmid pET28a-K61GQ96DS119A, recombinant plasmid pET28a-K61RQ96DS119A, recombinant plasmid pET28a-

H58AK61GQ96DS119A, recombinant plasmid pET28a-H58AK61RQ96DS119A, recombinant plasmid pET28a-M94K or recombinant plasmid pET28a-I155R proposed in examples.

The recombinant microorganism is a recombinant bacterium obtained by inserting the recombinant vector into an original microorganism.

The original microorganism can be *Escherichia coli*.

Specifically, the *Escherichia coli* can be *Escherichia coli* BL21 (DE3).

The transgenic cell line can be obtained by transforming the recombinant vector into recipient cells. The transgenic cell line is a non-plant propagative material.

Use of the protein as described above, the nucleic acid molecule as described above, or the expression cassette, the recombinant vector, the recombinant microorganism or the transgenic cell line comprising the nucleic acid molecule as described above in the preparation of DNA polymerase is also within the scope of the present disclosure.

According to the use as described above, the DNA polymerase has reduced exonuclease activity compared to the phi29 DNA polymerase, where the exonuclease activity is 3'-5'exonuclease activity.

Use of the protein as described above, the nucleic acid molecule as described above, or the expression cassette, the recombinant vector, the recombinant microorganism or the transgenic cell line comprising the nucleic acid molecule as described above in PCR amplification is also within the scope of the present disclosure.

Use of the protein as described above, the nucleic acid molecule as described above, or the expression cassette, the recombinant vector, the recombinant microorganism or the transgenic cell line comprising the nucleic acid molecule as described above in sequencing is also within the scope of the present disclosure.

Use of the protein as described above, the nucleic acid molecule as described above, or the expression cassette, the recombinant vector, the recombinant microorganism or the transgenic cell line comprising the nucleic acid molecule as described above in the preparation of a sequencing product is also within the scope of the present disclosure.

According to the use as described above, the sequencing product is a kit.

The present inventors after a great many experiments have prepared a series of recombinant phi29 DNA polymerases with significantly reduced 3'-5'exonuclease activity by point-mutating the existing phi29 DNA polymerase. Such recombinant phi29 DNA polymerases not only can ensure high fidelity, but also will not digest primers thus preventing the non-specific binding between the primers and target sequences. Use of the recombinant phi29 DNA polymerases prepared in the present disclosure for amplification and sequencing can ensure DNAs replicate effectively and persistently, with high efficiency.

BRIEF DESCRIPTION OF THE DRAWINGS

FIG. 1 shows the detection results of 3'-5'exonuclease activity of recombinant phi29 DNA polymerases.

DETAILED DESCRIPTION

The vector pET28a (+) is a product of Novagen. Reaction buffer 10×phi29 is a product of NEB (Catalog number: B0269S). Microplate reader is purchased from BioTek.

Affinity solution A: an aqueous solution containing 20 mM Tris-HCl, 500 mM NaCl, 20 mM Imidazole and 62.5 g/L Glycerol, pH 7.9.

Affinity solution B: an aqueous solution containing 20 mM Tris-HCl, 500 mM NaCl, 500 mM Imidazole and 62.5 g/L Glycerol, pH 7.9.

SPA buffer: an aqueous solution containing 20 mM Tris-HCl, 150 mM NaCl and 62.5 g/L Glycerol, pH 7.5.

SPB buffer: an aqueous solution containing 20 mM Tris-HCl, 1 M NaCl and 62.5 g/L Glycerol, pH 7.5.

TE buffer: an aqueous solution containing 20 mM Tris-HCl and 62.5 g/L Glycerol, pH 7.5.

Example 1. Preparation of phi29 DNA Polymerase and Recombinant phi29 DNA Polymerases 1.1 Construction of a recombinant plasmid 1.1.1 Construction of recombinant plasmid pET28a-WT 1.1.1.1 Recombinant plasmid pUC57-WT was synthesized by GenScript biotechnology Co. Ltd., which is formed by inserting a double-stranded DNA molecule into a restriction endonuclease recognition site of pUC57 plasmid DNA purchased from GenScript biotechnology Co. Ltd. (Catalog number: SD1176). The inserted double-stranded DNA molecule has a nucleotide sequence as shown in SEQ ID NO: 1 in the sequence listing.

1.1.1.2 The recombinant plasmid pUC57-WT was digested with restriction endonucleases NdeI and BamHI, and a fragment of about 1719 bp was recovered.

1.1.1.3 The vector pET28a (+) was digested with restriction endonucleases NdeI and BamHI, and a vector backbone of about 5300 bp was recovered.

1.1.1.4 The digested fragment was ligated to the vector backbone, thus obtaining the recombinant plasmid pET28a-WT.

Based on the results of sequencing, the recombinant plasmid pET28a-WT has a structure formed by replacing the small DNA fragment between the recognition sequence NdeI and the recognition sequence BamHI of the vector pET28a (+) with a double-stranded DNA molecule, where the double-stranded DNA molecule was fused with the encoding sequence of His-tag (consisting of 6 histidine residues) in the vector backbone, thus obtaining a fusion gene which can express a fusion protein 1 containing the His-tag. The fusion gene has a sequence as shown in SEQ ID NO: 3 in the sequence listing. The fusion protein 1 has a sequence as shown in SEQ ID NO: 4 in the sequence listing.

1.1.2 Construction of recombinant plasmid pET28a-H58A

The recombinant plasmid pET28a-H58A was constructed according to the method in 1.1.1. For the recombinant plasmid pET28a-H58A, a double-stranded DNA molecule to be inserted was fused with the encoding sequence of His-tag (consisting of 6 histidine residues) in the vector backbone of the vector pET28a (+), thus forming a fusion gene which can express a fusion protein 2, where the fusion protein 2 is similar to the fusion protein 1 except for substitution of histidine residue at position 78 of the fusion protein 1 with an alanine residue.

1.1.3 Construction of recombinant plasmid pET28a-K61G

The recombinant plasmid pET28a-K61G was constructed according to the method in 1.1.1. For the recombinant plasmid pET28a-K61G, a double-stranded DNA molecule to be inserted was fused with the encoding sequence of His-tag (consisting of 6 histidine residues) in the vector backbone of the vector pET28a (+), thus forming a fusion gene which can express a fusion protein 3, where the fusion protein 3 is similar to the fusion protein 1 except for substitution of lysine residue at position 81 of the fusion protein 1 with a glycine residue.

1.1.4 Construction of recombinant plasmid pET28a-K61R

The recombinant plasmid pET28a-K61R was constructed according to the method in 1.1.1. For the recombinant plasmid pET28a-K61R, a double-stranded DNA molecule to be inserted was fused with the encoding sequence of His-tag (consisting of 6 histidine residues) in the vector backbone of the vector pET28a (+), thus forming a fusion gene which can express a fusion protein 4, where the fusion protein 4 is similar to the fusion protein 1 except for substitution of lysine residue at position 81 of the fusion protein 1 with an arginine residue.

1.1.5 Construction of recombinant plasmid pET28a-Q96D

The recombinant plasmid pET28a-Q96D was constructed according to the method in 1.1.1. For the recombinant plasmid pET28a-Q96D, a double-stranded DNA molecule to be inserted was fused with the encoding sequence of His-tag (consisting of 6 histidine residues) in the vector backbone of the vector pET28a (+), thus forming a fusion gene which can express a fusion protein 5, where the fusion protein 5 is similar to the fusion protein 1 except for substitution of glutamine residue at position 116 of the fusion protein 1 with an aspartic acid residue.

1.1.6 Construction of recombinant plasmid pET28a-S119A

The recombinant plasmid pET28a-S119A was constructed according to the method in 1.1.1. For the recombinant plasmid pET28a-S119A, a double-stranded DNA molecule to be inserted was fused with the encoding sequence of His-tag (consisting of 6 histidine residues) in the vector backbone of the vector pET28a (+), thus forming a fusion gene which can express a fusion protein 6, where the fusion protein 6 is similar to the fusion protein 1 except for substitution of serine residue at position 139 of the fusion protein 1 with an alanine residue.

1.1.7 Construction of recombinant plasmid pET28a-H58AK61G

The recombinant plasmid pET28a-H58AK61G was constructed according to the method in 1.1.1. For the recombinant plasmid pET28a-H58AK61G, a double-stranded DNA molecule to be inserted was fused with the encoding sequence of His-tag (consisting of 6 histidine residues) in the vector backbone of the vector pET28a (+), thus forming a fusion gene which can express a fusion protein 7, where the fusion protein 7 is similar to the fusion protein 1 except for substitution of histidine residue at position 78 of the fusion protein 1 with an alanine residue and substitution of lysine residue at position 81 of the fusion protein 1 with a glycine residue.

1.1.8 Construction of recombinant plasmid pET28a-H58AK61R

The recombinant plasmid pET28a-H58AK61R was constructed according to the method in 1.1.1. For the recombinant plasmid pET28a-H58AK61R, a double-stranded DNA molecule to be inserted was fused with the encoding sequence of His-tag (consisting of 6 histidine residues) in the vector backbone of the vector pET28a (+), thus forming a fusion gene which can express a fusion protein 8, where the fusion protein 8 is similar to the fusion protein 1 except for substitution of histidine residue at position 78 of the fusion protein 1 with an alanine residue and substitution of lysine residue at position 81 of the fusion protein 1 with an arginine residue.

1.1.9 Construction of recombinant plasmid pET28a-H58AQ96D

The recombinant plasmid pET28a-H58AQ96D was constructed according to the method in 1.1.1. For the recombinant plasmid pET28a-H58AQ96D, a double-stranded DNA molecule to be inserted was fused with the encoding sequence of His-tag (consisting of 6 histidine residues) in the vector backbone of the vector pET28a (+), thus forming a fusion gene which can express a fusion protein 9, where the fusion protein 9 is similar to the fusion protein 1 except for substitution of histidine residue at position 78 of the fusion protein 1 with an alanine residue and substitution of glutamine residue at position 116 of the fusion protein 1 with an aspartic acid residue.

1.1.10 Construction of recombinant plasmid pET28a-H58AS119A

The recombinant plasmid pET28a-H58AS119A was constructed according to the method in 1.1.1. For the recombinant plasmid pET28a-H58AS119A, a double-stranded DNA molecule to be inserted was fused with the encoding sequence of His-tag (consisting of 6 histidine residues) in the vector backbone of the vector pET28a (+), thus forming a fusion gene which can express a fusion protein 10, where the fusion protein 10 is similar to the fusion protein 1 except for substitution of histidine residue at position 78 of the fusion protein 1 with an alanine residue and substitution of serine residue at position 139 of the fusion protein 1 with an alanine residue.

1.1.11 Construction of recombinant plasmid pET28a-K61GQ96D

The recombinant plasmid pET28a-K61GQ96D was constructed according to the method in 1.1.1. For the recombinant plasmid pET28a-K61GQ96D, a double-stranded DNA molecule to be inserted was fused with the encoding sequence of His-tag (consisting of 6 histidine residues) in the vector backbone of the vector pET28a (+), thus forming a fusion gene which can express a fusion protein 11, where the fusion protein 11 is similar to the fusion protein 1 except for substitution of lysine residue at position 81 of the fusion protein 1 with a glycine residue and substitution of glutamine residue at position 116 of the fusion protein 1 with an aspartic acid residue.

1.1.12 Construction of recombinant plasmid pET28a-K61GS119A

The recombinant plasmid pET28a-K61GS119A was constructed according to the method in 1.1.1. For the recombinant plasmid pET28a-K61GS119A, a double-stranded DNA molecule to be inserted was fused with the encoding sequence of His-tag (consisting of 6 histidine residues) in the vector backbone of the vector pET28a (+), thus forming a fusion gene which can express a fusion protein 12, where the fusion protein 12 is similar to the fusion protein 1 except for substitution of lysine residue at position 81 of the fusion protein 1 with a glycine residue and substitution of serine residue at position 139 of the fusion protein 1 with an alanine residue.

1.1.13 Construction of recombinant plasmid pET28a-K61RQ96D

The recombinant plasmid pET28a-K61RQ96D was constructed according to the method in 1.1.1. For the recombinant plasmid pET28a-K61RQ96D, a double-stranded DNA molecule to be inserted was fused with the encoding sequence of His-tag (consisting of 6 histidine residues) in the vector backbone of the vector pET28a (+), thus forming a fusion gene which can express a fusion protein 13, where the fusion protein 13 is similar to the fusion protein 1 except for substitution of lysine residue at position 81 of the fusion protein 1 with an arginine residue and substitution of glutamine residue at position 116 of the fusion protein 1 with an aspartic acid residue.

1.1.14 Construction of recombinant plasmid pET28a-K61RS119A

The recombinant plasmid pET28a-K61RS119A was constructed according to the method in 1.1.1. For the recombinant plasmid pET28a-K61RS119A, a double-stranded DNA molecule to be inserted was fused with the encoding sequence of His-tag (consisting of 6 histidine residues) in the vector backbone of the vector pET28a (+), thus forming a fusion gene which can express a fusion protein 14, where the fusion protein 14 is similar to the fusion protein 1 except for substitution of lysine residue at position 81 of the fusion protein 1 with an arginine residue and substitution of serine residue at position 139 of the fusion protein 1 with an alanine residue.

1.1.15 Construction of recombinant plasmid pET28a-Q96DS119A

The recombinant plasmid pET28a-Q96DS119A was constructed according to the method in 1.1.1. For the recombinant plasmid pET28a-Q96DS119A, a double-stranded DNA molecule to be inserted was fused with the encoding sequence of His-tag (consisting of 6 histidine residues) in the vector backbone of the vector pET28a (+), thus forming a fusion gene which can express a fusion protein 15, where the fusion protein 15 is similar to the fusion protein 1 except for substitution of glutamine residue at position 116 of the fusion protein 1 with an aspartic acid residue and substitution of serine residue at position 139 of the fusion protein 1 with an alanine residue.

1.1.16 Construction of recombinant plasmid pET28a-H58AK61GQ96D

The recombinant plasmid pET28a-H58AK61GQ96D was constructed according to the method in 1.1.1. For the recombinant plasmid pET28a-H58AK61GQ96D, a double-stranded DNA molecule to be inserted was fused with the encoding sequence of His-tag (consisting of 6 histidine residues) in the vector backbone of the vector pET28a (+), thus forming a fusion gene which can express a fusion protein 16, where the fusion protein 16 is similar to the fusion protein 1 except for substitution of histidine residue at position 78 of the fusion protein 1 with an alanine residue, substitution of lysine residue at position 81 of the fusion protein 1 with a glycine residue, and substitution of glutamine residue at position 116 of the fusion protein 1 with an aspartic acid residue.

1.1.17 Construction of recombinant plasmid pET28a-H58AK61GS119A

The recombinant plasmid pET28a-H58AK61GS119A was constructed according to the method in 1.1.1. For the recombinant plasmid pET28a-H58AK61GS119A, a double-stranded DNA molecule to be inserted was fused with the encoding sequence of His-tag (consisting of 6 histidine residues) in the vector backbone of the vector pET28a (+), thus forming a fusion gene which can express a fusion protein 17, where the fusion protein 17 is similar to the fusion protein 1 except for substitution of histidine residue at position 78 of the fusion protein 1 with an alanine residue, substitution of lysine residue at position 81 of the fusion protein 1 with a glycine residue, and substitution of serine residue at position 139 of the fusion protein 1 with an alanine residue.

1.1.18 Construction of recombinant plasmid pET28a-H58AK61RQ96D

The recombinant plasmid pET28a-H58AK61RQ96D was constructed according to the method in 1.1.1. For the recombinant plasmid pET28a-H58AK61RQ96D, a double-stranded DNA molecule to be inserted was fused with the encoding sequence of His-tag (consisting of 6 histidine residues) in the vector backbone of the vector pET28a (+), thus forming a fusion gene which can express a fusion protein 18, where the fusion protein 18 is similar to the fusion protein 1 except for substitution of histidine residue at position 78 of the fusion protein 1 with an alanine residue, substitution of lysine residue at position 81 of the fusion protein 1 with an arginine residue, and substitution of glutamine residue at position 116 of the fusion protein 1 with an aspartic acid residue.

1.1.19 Construction of recombinant plasmid pET28a-H58AK61RS119A

The recombinant plasmid pET28a-H58AK61RS119A was constructed according to the method in 1.1.1. For the recombinant plasmid pET28a-H58AK61RS119A, a double-stranded DNA molecule to be inserted was fused with the encoding sequence of His-tag (consisting of 6 histidine residues) in the vector backbone of the vector pET28a (+), thus forming a fusion gene which can express a fusion protein 19, where the fusion protein 19 is similar to the fusion protein 1 except for substitution of histidine residue at position 78 of the fusion protein 1 with an alanine residue, substitution of lysine residue at position 81 of the fusion protein 1 with an arginine residue, and substitution of serine residue at position 139 of the fusion protein 1 with an alanine residue.

1.1.20 Construction of recombinant plasmid pET28a-K61GQ96DS119A

The recombinant plasmid pET28a-K61GQ96DS119A was constructed according to the method in 1.1.1. For the recombinant plasmid pET28a-K61GQ96DS119A, a double-stranded DNA molecule to be inserted was fused with the encoding sequence of His-tag (consisting of 6 histidine residues) in the vector backbone of the vector pET28a (+), thus forming a fusion gene which can express a fusion protein 20, where the fusion protein 20 is similar to the fusion protein 1 except for substitution of lysine residue at position 81 of the fusion protein 1 with a glycine residue, substitution of glutamine residue at position 116 of the fusion protein 1 with an aspartic acid residue, and substitution of serine residue at position 139 of the fusion protein 1 with an alanine residue.

1.1.21 Construction of recombinant plasmid pET28a-K61RQ96DS119A

The recombinant plasmid pET28a-K61RQ96DS119A was constructed according to the method in 1.1.1. For the recombinant plasmid pET28a-K61RQ96DS119A, a double-stranded DNA molecule to be inserted was fused with the encoding sequence of His-tag (consisting of 6 histidine residues) in the vector backbone of the vector pET28a (+), thus forming a fusion gene which can express a fusion protein 21, where the fusion protein 21 is similar to the fusion protein 1 except for substitution of lysine residue at position 81 of the fusion protein 1 with an arginine residue, substitution of glutamine residue at position 116 of the fusion protein 1 with an aspartic acid residue, and substitution of serine residue at position 139 of the fusion protein 1 with an alanine residue.

1.1.22 Construction of recombinant plasmid pET28a-H58AK61GQ96DS119A

The recombinant plasmid pET28a-H58AK61GQ96DS119A was constructed according to the method in 1.1.1. For the recombinant plasmid pET28a-H58AK61GQ96DS119A, a double-stranded DNA molecule to be inserted was fused with the encoding sequence of His-tag (consisting of 6 histidine residues) in the vector backbone of the vector pET28a (+), thus forming a fusion gene which can express a fusion protein 22, where the fusion protein 22 is similar to the fusion protein 1 except for substitution of histidine residue at position 78 of the fusion protein 1 with an alanine residue, substitution of lysine residue at position 81 of the fusion protein 1 with a glycine residue, substitution of glutamine residue at position 116 of the fusion protein 1 with an aspartic acid residue, and substitution of serine residue at position 139 of the fusion protein 1 with an alanine residue.

1.1.23 Construction of recombinant plasmid pET28a-H58AK61RQ96DS119A

The recombinant plasmid pET28a-H58AK61RQ96DS119A was constructed according to the method in 1.1.1. For the recombinant plasmid pET28a-H58AK61RQ96DS119A, a double-stranded DNA molecule to be inserted was fused with the encoding sequence of His-tag (consisting of 6 histidine residues) in the vector backbone of the vector pET28a (+), thus forming a fusion gene which can express a fusion protein 23, where the fusion protein 23 is similar to the fusion protein 1 except for substitution of histidine residue at position 78 of the fusion protein 1 with an alanine residue, substitution of lysine residue at position 81 of the fusion protein 1 with an arginine residue, substitution of glutamine residue at position 116 of the fusion protein 1 with an aspartic acid residue, and substitution of serine residue at position 139 of the fusion protein 1 with an alanine residue.

1.1.24 Construction of recombinant plasmid pET28a-M94K

The recombinant plasmid pET28a-M94K was constructed according to the method in 1.1.1. For the recombinant plasmid pET28a-M94K, a double-stranded DNA molecule to be inserted was fused with the encoding sequence of His-tag (consisting of 6 histidine residues) in the vector backbone of the vector pET28a (+), thus forming a fusion gene which can express a fusion protein 24, where the fusion protein 24 is similar to the fusion protein 1 except for substitution of methionine residue at position 114 of the fusion protein 1 with a lysine residue.

1.1.25 Construction of recombinant plasmid pET28a-I155R

The recombinant plasmid pET28a-I155R was constructed according to the method in 1.1.1. For the recombinant plasmid pET28a-I155R, a double-stranded DNA molecule to be inserted was fused with the encoding sequence of His-tag (consisting of 6 histidine residues) in the vector backbone of the vector pET28a (+), thus forming a fusion gene which can express a fusion protein 25, where the fusion protein 25 is similar to the fusion protein 1 except for substitution of isoleucine residue at position 175 of the fusion protein 1 with an arginine residue.

1.2 Expression and purification of recombinant phi29 DNA polymerases

The recombinant phi29 DNA polymerase 1 is expressed and purified according to the following steps.

1.2.1 The recombinant plasmid pET28a-WT was transformed into *Escherichia coli* BL21 (DE3) to obtain a recombinant bacterium, named as BL21 (DE3)-WT.

1.2.2 The obtained monoclone BL21(DE3)-WT was seeded into 5 mL of LB liquid medium (containing 50 μg/mL kanamycin), followed by incubated with shaking at 37° C. and 200 rpm for 12 hours to obtain a bacteria solution.

1.2.3 The bacteria solution was seeded into 1.5 L LB liquid medium (containing 50 μg/mL kanamycin) at a volume ratio of 1:100, and incubated with shaking at 37° C. and 200 rpm until the $OD_{600\ nm}$ reaches 0.6. After that 0.5 mM of Isopropyl-beta-D-thiogalactopyranoside (IPTG) was added, the bacteria solution was incubated with shaking at 16° C. and 200 rpm for another 12 hours, centrifuged at 4° C. and 8000 rpm for 10 minutes, and the bacterial pellet was collected.

1.2.4 After the step 1.2.3, the affinity solution A was added to resuspend the obtained bacterial pellet, incubated on ice for 30 minutes, ultrasonicated in ice-water bath by using the ultrasonic cell disruptor with 06 probe from Ningbo Scientz Biote.Co., Ltd. under 40% ultrasonic power through a cycle procedure (2 seconds of breaking and 3 seconds of pausing, in total of 30 minutes), followed by centrifugation at 4° C. and 15000 rpm for 30 minutes, and the supernatant was collected.

1.2.5 After the step 1.2.4, the collected supernatant was vacuum-filtered through a 0.45 μm filter membrane, thus harvesting a crude solution of recombinant phi29 DNA polymerase 1.

1.2.6 The crude solution of recombinant phi29 DNA polymerase 1 was subjected to purification by using HisTrap Fast Flow from General Electric (GE) Company (Catalog number: 17-5255-01) according to the following steps.

Step a. The working pump and system of the AKTA protein purification system were washed with ultrapure water according to the operation procedure, and then HisTrap Fast Flow was equipped under a flow rate of 0.5 mL/min, which was washed with 5 column volumes of ultrapure water.

Step b. After the step a, pumps A1 and A2 were respectively washed with the affinity solution A, and pump B1 was washed with the affinity solution B.

Step c. After the step b, the HisTrap Fast Flow was equilibrated with 5 column volumes of affinity solution A at a flow rate of 5 mL/min.

Step d. After the step c, the crude solution of recombinant phi29 DNA polymerase 1 was loaded into the HisTrap Fast Flow through the pump A2 at a flow rate of 3 mL/min Step e. After the step d, the HisTrap Fast Flow was washed again with 10 column volumes of affinity solution A at a flow rate of 5 mL/min, and the eluted solution was measured under 280 nm, with an absorbance similar to that of the affinity solution A.

Step f. After the step e, the HisTrap Fast Flow was subjected to a linear gradient elution with an eluent of the affinity solution A and the affinity solution B at a flow rate of 10 mL/min. The eluted solution having an ultraviolet absorption peak higher than 50 mAu relative to the baseline is collected and combined, thus harvesting a solution 1 of recombinant phi29 DNA polymerase 1. The gradient elution procedure includes: the affinity solution B in an elution concentration uniformly increasing from 0% to 100% by volume, the affinity solution A in an elution concentration uniformly decreasing from 100% to 0% by volume, and 20 column volumes of linear gradient eluent. The detection wavelength was 280 nm.

1.2.7 After the step 1.2.6, HiTrap Q HP pre-packed column from GE (Catalog number: 17-1154-01) was used for purification according to the following steps.

Step a. The working pump and system of the AKTA protein purification system were washed with ultrapure water according to the operation procedure, and then the HiTrap Q HP pre-packed column was equipped under a flow rate of 0.5 mL/min, which was washed with 5 column volumes of ultrapure water.

Step b. After the step a, the pumps A1 and A2 were respectively washed with the SPA buffer, and the pump B1 was washed with the SPB buffer.

Step c. After the step b, the HiTrap Q HP pre-packed column was equilibrated with 10 column volumes of mixed buffer (consisting of 41 parts of SPB buffer by volume and 59 parts of SPA buffer by volume) at a flow rate of 5 mL/min. The liquid outlet was adjusted to Outlet1 so as to wash the pipe. The mAu value was corrected to be zero after equilibration. The detection wavelength was 280 nm.

Step d. After the step c, the solution 1 of recombinant phi29 DNA polymerase 1 was loaded into the HiTrap Q HP pre-packed column through the pump A2 at a flow rate of 5 mL/min. The eluted solution was collected via the Outlet1 when the UV detection value reaches 50 mAu, and the collection was stopped when the UV detection value is lower than 50 mAu, thus obtaining a solution 2 of recombinant phi29 DNA polymerase 1. The detection wavelength was 280 nm.

1.2.8 After the step 1.2.7, HiTrap SP HP pre-packed column from GE (Catalog number: 17-1152-01) was used for further purification according to the following steps.

Step a. The working pump and system of the AKTA protein purification system were washed with ultrapure water according to the operation procedure, and then the HiTrap SP HP pre-packed column was equipped under a flow rate of 0.5 mL/min, which was washed with 5 column volumes of ultrapure water.

Step b. After the step a, the pumps A1 and A2 were respectively washed with the SPA buffer, and the pump B1 was washed with the SPB buffer.

Step c. After the step b, the HiTrap SP HP pre-packed column was equilibrated with 5 column volumes of SPA buffer at a flow rate of 5 mL/min. The liquid outlet was adjusted to Outlet1 so as to wash the pipe. The mAu value was corrected to be zero after equilibration. The detection wavelength was 280 nm.

Step d. The taken solution 2 of recombinant phi29 DNA polymerase 1 was diluted into 3.33 times of volume with TE buffer and then vacuum-filtered with 0.22 μm filter membrane to obtain a diluted solution 2.

Step e. After the steps c and d, the diluted solution 2 was loaded into the HiTrap SP HP pre-packed column through the pump A2 at a flow rate of 5 mL/min, and the liquid outlet was set to Waste.

Step f. After the step e, the HiTrap SP HP pre-packed column was washed with 15 column volumes of SPA buffer at a flow rate 5 mL/min, and the liquid outlet was adjusted to Outlet1 so as to wash the pipe.

Step g. After the step f, the HiTrap SP HP pre-packed column was subjected to a linear gradient elution with an eluent of the SPB buffer and the SPA buffer at a flow rate of 5 mL/min. The eluted solution was collected via Outlet1 as soon as the conductivity reaches 17.8 mS/cm and the collection was stopped when the conductivity was 29 mS/cm, thus obtaining the pure recombinant phi29 DNA polymerase 1. The gradient elution procedure includes: the SPB buffer in an elution concentration uniformly increasing from 0% to 35% by volume, the SPA buffer in an elution concentration uniformly decreasing from 100% to 65% by volume, and 10.5 column volumes of linear gradient eluent. The detection wavelength was 280 nm.

A pure recombinant phi29 DNA polymerase 2, a pure recombinant phi29 DNA polymerase 3, a pure recombinant phi29 DNA polymerase 4, a pure recombinant phi29 DNA polymerase 5, a pure recombinant phi29 DNA polymerase 6, a pure recombinant phi29 DNA polymerase 7, a pure recombinant phi29 DNA polymerase 8, a pure recombinant phi29 DNA polymerase 9, a pure recombinant phi29 DNA polymerase 10, a pure recombinant phi29 DNA polymerase 11, a pure recombinant phi29 DNA polymerase 12, a pure recombinant phi29 DNA polymerase 13, a pure recombinant phi29 DNA polymerase 14, a pure recombinant phi29 DNA polymerase 15, a pure recombinant phi29 DNA polymerase 16, a pure recombinant phi29 DNA polymerase 17, a pure recombinant phi29 DNA polymerase 18, a pure recombinant phi29 DNA polymerase 19, a pure recombinant phi29 DNA polymerase 20, a pure recombinant phi29 DNA polymerase 21, a pure recombinant phi29 DNA polymerase 22, a pure recombinant phi29 DNA polymerase 23, a pure recombinant phi29 DNA polymerase 24 and a pure recombinant phi29 DNA polymerase 25 were respectively obtained according to the method as described above except for the replacement of the recombinant plasmid pET28a-WT with the recombinant plasmid pET28a-H58A, the recombinant plasmid pET28a-K61G, the recombinant plasmid pET28a-K61R, the recombinant plasmid pET28a-Q96D, the recombinant plasmid pET28a-S119A, the recombinant plasmid pET28a-H58AK61G, the recombinant plasmid pET28a-H58AK61R, the recombinant plasmid pET28a-H58AQ96D, the recombinant plasmid pET28a-H58AS119A, the recombinant plasmid pET28a-K61GQ96D, the recombinant plasmid pET28a-K61GS119A, the recombinant plasmid pET28a-K61RQ96D, the recombinant plasmid pET28a-K61RS119A, the recombinant plasmid pET28a-Q96DS119A, the recombinant plasmid pET28a-H58AK61GQ96D, the recombinant plasmid pET28a-H58AK61GS119A, the recombinant plasmid pET28a-H58AK61RQ96D, the recombinant plasmid pET28a-H58AK61RS119A, the recombinant plasmid pET28a-K61GQ96DS119A, the recombinant plasmid pET28a-K61RQ96DS119A, the recombinant plasmid pET28a-H58AK61GQ96DS119A, the recombinant plasmid pET28a-H58AK61RQ96DS119A, the recombinant plasmid pET28a-M94K and the recombinant plasmid pET28a-I155R respectively.

The obtained recombinant phi29 DNA polymerases were subjected to SDS-PAGE respectively. The results have showed that the recombinant phi29 DNA polymerases each have a molecular weight of 67 kDa.

Example 2. Detection of 3'-5'Exonuclease Activity of Recombinant phi29 DNA Polymerases The detection principle and method are described as below. Phi29 DNA polymerase has 3'-5'exonuclease activity, thus being capable of cutting the quenching group at the 3' end of the single-stranded DNA substrate under a suitable buffer system. According to fluorescence resonance energy transfer, the fluorescent group-quenching group pair usually can provide a low background signal and changed sensitive fluorescence intensity when the quenching group is transferred out of a resonance distance with the fluorescent group. The fluorescence-labelled substrate provided in this example is 5'-RoxATCAGCAGGCCACACGTTAAAGACABHQ2-3', a 25-mer, which is a single-stranded DNA having a Rox fluorescent group at the 5' end and a BHQ2 quenching group at the 3' end, without sequence specificity. The fluorescence-labelled substrate can exhibit a 582 nm of excitation wavelength and a 618 nm of emission wavelength through detection of a microplate reader. Thus, the fluorescence value of the Rox fluorescent group at the 5' end will increase significantly when the phi29 DNA polymerase exhibits its 3'-5'exonuclease activity on the BHQ2 quenching group of the fluorescence-labelled substrate. The fluorescence value will change linearly with time by adjusting the concentration of phi29 DNA polymerase and the reaction time. Faster the fluorescence value changes, larger the slope in the linear equation is, indicating stronger 3'-5'exonuclease activity of phi29 DNA polymerase. After a great many experiments, it is determined that the concentration of phi29 DNA polymerase is 0.004 mg/mL and the concentration of fluorescence-labelled substrate is 100 nM in the reaction system suitable for detection of the 3'-5'exonuclease activity of phi29 DNA polymerase, as well the reaction time is 20 minutes.

The 3'-5'exonuclease activity of the phi29 DNA polymerase to be tested was detected according to the principle as described above. The phi29 DNA polymerase to be tested includes the recombinant phi29 DNA polymerase 1, the recombinant phi29 DNA polymerase 2, the recombinant phi29 DNA polymerase 3, the recombinant phi29 DNA polymerase 4, the recombinant phi29 DNA polymerase 5, the recombinant phi29 DNA polymerase 6, the recombinant phi29 DNA polymerase 7, the recombinant phi29 DNA polymerase 8, the recombinant phi29 DNA polymerase 9, the recombinant phi29 DNA polymerase 10, the recombinant phi29 DNA polymerase 11, the recombinant phi29 DNA polymerase 12, the recombinant phi29 DNA polymerase 13, the recombinant phi29 DNA polymerase 14, the recombinant phi29 DNA polymerase 15, the recombinant phi29 DNA polymerase 16, the recombinant phi29 DNA polymerase 17, the recombinant phi29 DNA polymerase 18, the recombinant phi29 DNA polymerase 19, the recombinant phi29 DNA polymerase 20, the recombinant phi29 DNA Polymerase 21, the recombinant phi29 DNA polymerase 22, the recombinant phi29 DNA polymerase 23, the recombinant phi29 DNA polymerase 24 and the recombinant phi29 DNA polymerase 25.

The experiment was repeated three times according to the following steps, with each experiment in triplicate.

2.1 Preparation of a reaction system

Reaction system 1 consists of phi29 DNA polymerase to be tested, fluorescence-labelled substrate, 10×phi29 reaction buffer and water. 50 μL of the reaction system 1 comprises 5 μL of 10×phi29 reaction buffer, phi29 DNA polymerase to be tested in a concentration of 0.004 mg/mL, fluorescence-labelled substrate in a concentration of 100 nM, with the balance of water.

The reaction system 2 consists of fluorescence-labelled substrate, 10×phi29 reaction buffer and water. 50 μL of the reaction system 2 comprises 5 μL of 10×phi29 reaction buffer, fluorescence-labelled substrate in a concentration of 100 nM, with the balance of water. The reaction system 2 is used as a negative control.

Because the phi29 DNA polymerase to be tested is a mesophilic DNA polymerase, it is necessary to ensure a rapid preparation of the reaction system 1 and the reaction system 2 on ice when needed.

2.2 The reaction system 1 or the reaction system 2 prepared in 2.1 was placed in the microplate reader at 25° C. for detection. The detection details includes: initial kinetics (30 seconds of plate-shaking before detection, data recorded once per minute), 20 minutes of detection time, 582 nm of excitation wavelength and 618 nm of emission wavelength. After the detection, a trend graph of signal change curve was plotted by using time as horizontal axis and fluorescence value as vertical axis, and a linear equation is further obtained.

Parts of experimental results are shown in FIG. 1, where WT refers to the recombinant phi29 DNA polymerase 1, K61G refers to the recombinant phi29 DNA polymerase 3, and Q96D refers to the recombinant phi29 DNA polymerase 5. The fluorescence value is in a linear increase at the detection time from 0 to 10 minutes. The 3'-5'exonuclease activity of phi29 DNA polymerase to be tested was evaluated depending on the slope in the linear equation, where a larger slope value indicates a stronger 3'-5'exonuclease activity. The results in FIG. 1 indicate that the 3'-5'exonuclease activity is strongest for the recombinant phi29 DNA polymerase 1, followed by the recombinant phi29 DNA polymerase 5, and then by the recombinant phi29 DNA polymerase 3.

The results have showed that the recombinant phi29 DNA polymerase 2, the recombinant phi29 DNA polymerase 3, the recombinant phi29 DNA polymerase 4, the recombinant phi29 DNA polymerase 5, the recombinant phi29 DNA polymerase 6, the recombinant phi29 DNA polymerase 7, the recombinant phi29 DNA polymerase 8, the recombinant phi29 DNA polymerase 9, the recombinant phi29 DNA polymerase 10, the recombinant phi29 DNA polymerase 11, the recombinant phi29 DNA polymerase 12, the recombinant phi29 DNA polymerase 13, the recombinant phi29 DNA polymerase 14, the recombinant phi29 DNA polymerase 15, the recombinant phi29 DNA polymerase 16, the recombinant phi29 DNA polymerase 17, the recombinant phi29 DNA polymerase 18, the recombinant phi29 DNA polymerase 19, the recombinant phi29 DNA polymerase 20, the recombinant phi29 DNA polymerase 21, the recombinant phi29 DNA polymerase 22, the recombinant phi29 DNA polymerase 23, the recombinant phi29 DNA polymerase 24 and the recombinant phi29 DNA polymerase 25 all have reduced 3'-5'exonuclease activity to some extent, compared with the recombinant phi29 DNA polymerase 1.

INDUSTRIAL APPLICATION

The experiments have proved that the recombinant phi29 DNA polymerases prepared in the present disclosure have reduced 3'-5'exonuclease activity relative to the phi29 DNA polymerase, which not only can ensure high fidelity, but also will not digest primers thus preventing the non-specific binding between the primers and target sequences. Use of the recombinant phi29 DNA polymerases prepared in the present disclosure for amplification and sequencing can ensure DNAs replicate effectively and continuously, with high efficiency

What is claimed is:

1. A protein selected from protein C1) or C2), wherein

C1) consists of at least one amino acid residue substitution(s) at position(s) selected from 61, 96, 58, 94, 119 and 155 and unchanged remaining amino acid residues relative to the amino acid sequence of a wild-type phi29 DNA polymerase of SEQ ID NO: 2, wherein the lysine residue at position 61 is substituted with a glycine residue or an arginine residue, the glutamine residue at position 96 is substituted with an aspartic acid residue, the histidine residue at position 58 is substituted with an alanine residue, the methionine residue at position 94 is substituted with a lysine residue, the serine residue at position 119 is substituted with an alanine residue, and the isoleucine residue at position 155 is substituted with an arginine residue, and C2) is a fusion protein formed by ligating with a tag at one or both of the N-terminus and the C-terminus of the protein C1), wherein the protein C1) or C2) has reduced 3'-5'exonuclease activity while ensuring high fidelity compared to the wild-type phi29 DNA polymerase.

2. A nucleic acid molecule encoding the protein as defined in claim 1.

3. A method for preparing a kit comprising:
utilizing the protein as defined in claim 1 for preparing the kit.

* * * * *